(12) United States Patent
Nakamura

(10) Patent No.: US 11,889,974 B2
(45) Date of Patent: Feb. 6, 2024

(54) ENDOSCOPE APPARATUS AND ENDOSCOPE APPARATUS OPERATION METHOD

(71) Applicant: OLYMPUS CORPORATION, Tokyo (JP)

(72) Inventor: Sho Nakamura, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 542 days.

(21) Appl. No.: 17/124,773

(22) Filed: Dec. 17, 2020

(65) Prior Publication Data

US 2021/0100427 A1 Apr. 8, 2021

Related U.S. Application Data

(63) Continuation of application No. PCT/JP2018/025368, filed on Jul. 4, 2018.

(51) Int. Cl.
*A61B 1/00* (2006.01)

(52) U.S. Cl.
CPC ...... *A61B 1/00006* (2013.01); *A61B 1/00025* (2013.01); *A61B 1/00096* (2013.01); *A61B 2562/0271* (2013.01)

(58) Field of Classification Search
CPC ............ A61B 1/00006; A61B 1/00025; A61B 1/00096; A61B 1/00188; A61B 1/00163; A61B 1/0019; A61B 1/04; A61B 1/045; A61B 1/0008; A61B 1/00097; A61B 1/12; A61B 1/128; A61B 1/0002; A61B 1/00112; A61B 1/00114; A61B 2562/0271; A61B 2562/0276
USPC .................................. 600/118, 167–168, 160
See application file for complete search history.

(56) References Cited

U.S. PATENT DOCUMENTS

2015/0084641 A1 3/2015 Kawakami et al.
2016/0331211 A1* 11/2016 Fujisawa ................ A61B 1/009

FOREIGN PATENT DOCUMENTS

| JP | 4339823 B2 | 10/2009 |
| JP | 2010-005180 A | 1/2010 |
| JP | 2015-062469 A | 4/2015 |
| JP | 2018-082804 A | 5/2018 |
| WO | 2018/011857 A1 | 1/2018 |

OTHER PUBLICATIONS

International Search Report dated Sep. 4, 2018 received in PCT/JP2018/025368.
English abstract only of JP 2006-000660 A.

* cited by examiner

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An endoscope apparatus includes an endoscope having a lens, an actuator, and an endoscope memory, and a processor having a driving circuit and a processor memory and connected to the endoscope. The processor judges whether there is abnormality or not in at least one of the actuator or the driving circuit by using information on a signal transmitted from the driving circuit to the actuator, first judgement information read from the endoscope memory, and second judgement information read from the processor memory.

11 Claims, 5 Drawing Sheets

FIG. 4

|  | PROCESSOR MEMORY UNIT | ENDOSCOPE MEMORY UNIT | EXAMPLE |
|---|---|---|---|
| CONSTANT-VOLTAGE SIGNAL | VOLTAGE THRESHOLD | CURRENT THRESHOLD | DIFFERENTIAL AMPLIFICATION UNIT |
| CONSTANT-CURRENT SIGNAL | CURRENT THRESHOLD | VOLTAGE THRESHOLD | HALL DEVICE |
| VARIABLE-VOLTAGE /VARIABLE-CURRENT SIGNAL | — | VOLTAGE THRESHOLD, CURRENT THRESHOLD | VCM |

FIG. 5

| | | |
|---|---|---|
| ENDOSCOPE MEMORY UNIT | VOLTAGE THRESHOLD FOR VCM | DURATION FOR VOLTAGE IN VCM |
| | CURRENT THRESHOLD FOR VCM | DURATION FOR CURRENT IN VCM |
| | VOLTAGE THRESHOLD FOR HALL DEVICE | DURATION FOR VOLTAGE IN HALL DEVICE |
| | CURRENT THRESHOLD FOR DIFFERENTIAL AMPLIFICATION UNIT | DURATION FOR CURRENT IN DIFFERENTIAL AMPLIFICATION UNIT |
| | TEMPERATURE THRESHOLD | DURATION FOR TEMPERATURE |
| PROCESSOR MEMORY UNIT | CURRENT THRESHOLD FOR HALL DEVICE | DURATION FOR CURRENT IN HALL DEVICE |
| | VOLTAGE THRESHOLD FOR DIFFERENTIAL AMPLIFICATION UNIT | DURATION FOR VOLTAGE IN DIFFERENTIAL AMPLIFICATION UNIT |

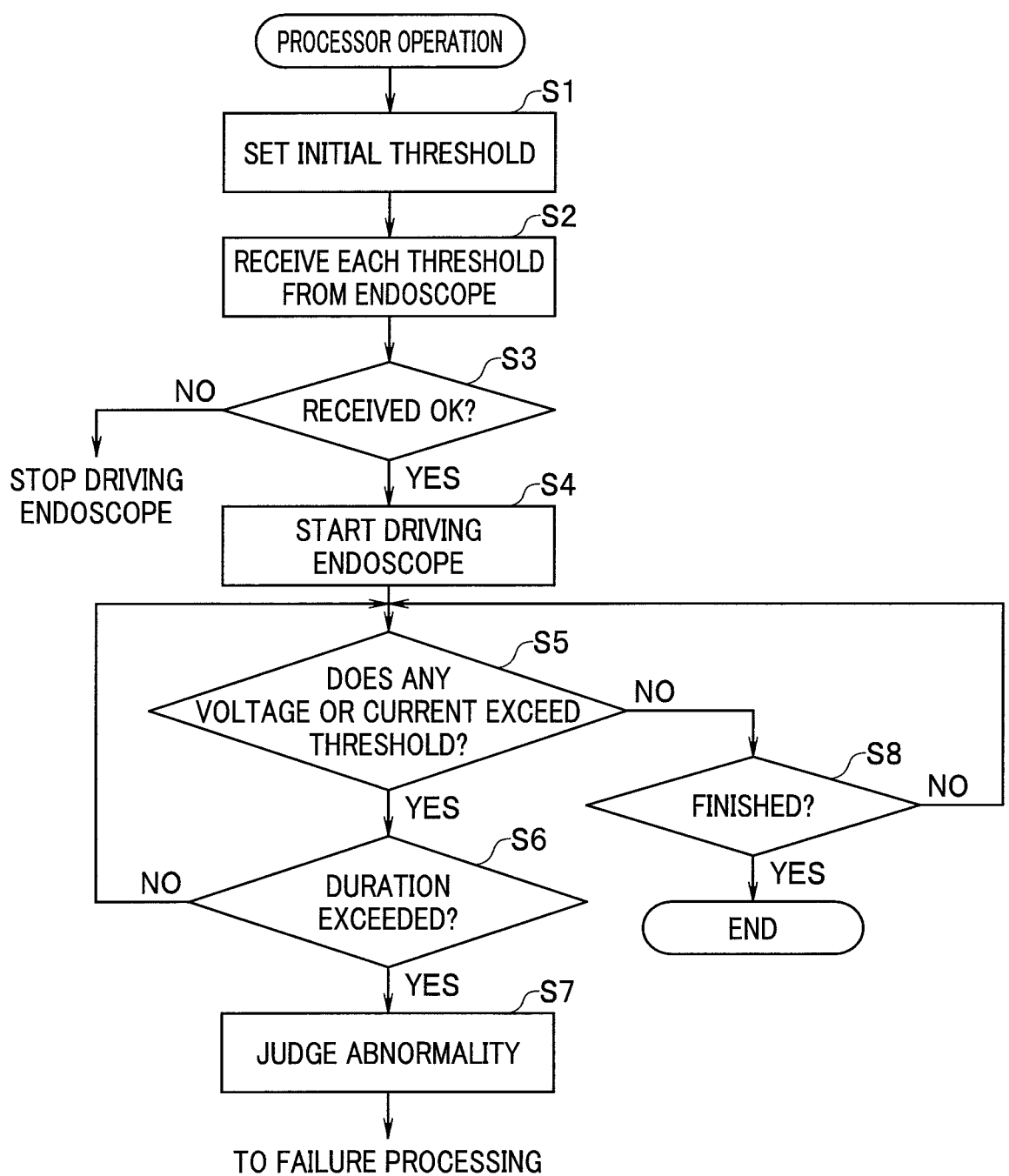

ENDOSCOPE APPARATUS AND ENDOSCOPE APPARATUS OPERATION METHOD

CROSS REFERENCE TO RELATED APPLICATION

This application is a continuation application of PCT/JP2018/025368 filed on Jul. 4, 2018, the entire contents of which are incorporated herein by this reference.

BACKGROUND OF THE INVENTION

1. Field of the Invention

The present invention relates to an endoscope apparatus in which an endoscope including an actuator configured to drive a lens is driven by a processor, and an endoscope apparatus operation method.

2. Description of the Related Art

Conventionally, endoscope apparatuses have been used widely in various fields including the medical field, the industrial field, and the academic field. In the endoscope apparatuses thus used, in response to the need for improvement of optical performance, apparatuses including a mechanism to drive a lens have been proposed. More specifically, there is a configuration proposed such that an actuator configured to drive a lens is mounted in an endoscope and a driving circuit configured to drive the actuator by supplying power to the actuator is mounted in a processor.

For example, Japanese Patent No. 4339823 discloses a technique in which abnormality such as a short circuit, opening, and heat generation in an actuator mounted in an endoscope is detected by a processor connected to the endoscope. Here, the processor processes image pickup signals obtained by an image pickup device mounted in the endoscope. Then, judgement conditions such as a threshold for use in detecting abnormality are stored in the processor.

An endoscope and a processor are used in various combinations. For example, various types of endoscopes are connected to a single processor. The type of an actuator mounted in an endoscope varies depending on the type of an endoscope, or varies according to, for example, the size, etc. of an endoscope. When the type of an actuator changes, a voltage threshold and a current threshold based on which abnormality should be determined will also change.

A single endoscope is also connected to various kinds of processors. The type of a driving circuit mounted in a processor varies depending on the type of the processor. When the type of a driving circuit changes, a standard and accuracy, etc. of a signal transmitted from the driving circuit will also change.

SUMMARY OF THE INVENTION

An endoscope apparatus according to one embodiment of the present invention includes an endoscope, a processor to which the endoscope is connected, a lens arranged in the endoscope, an actuator arranged in the endoscope and configured to drive the lens, a driving circuit arranged in the processor and configured to drive the actuator by transmitting a signal to the actuator, a first memory arranged in the endoscope and configured to store first judgement information for use in judging abnormality of at least one of the actuator or the driving circuit, and a second memory arranged in the processor and configured to store second judgement information for use in judging abnormality of at least one of the actuator or the driving circuit, the second judgement information being different from the first judgement information, wherein the processor judges whether there is abnormality or not in at least one of the actuator or the driving circuit by using information on the signal transmitted from the driving circuit to the actuator, the first judgement information read from the first memory, and the second judgement information read from the second memory.

An endoscope apparatus operation method according to one embodiment of the present invention includes steps of causing an actuator arranged in an endoscope to drive a lens arranged in the endoscope, causing a driving circuit arranged in a processor connected to the endoscope to drive the actuator by transmitting a signal to the actuator, causing a first memory arranged in the endoscope to store first judgement information for use in judging abnormality of at least one of the actuator or the driving circuit, causing a second memory arranged in the processor to store second judgement information for use in judging abnormality of at least one of the actuator or the driving circuit, the second judgement information being different from the first judgement information, and causing the processor to judge whether there is abnormality or not in at least one of the actuator or the driving circuit by using information on the signal transmitted from the driving circuit to the actuator, the first judgement information read from the first memory, and the second judgement information read from the second memory.

BRIEF DESCRIPTION OF THE DRAWINGS

FIG. 4 is a table showing judgement information stored in an endoscope memory unit and a processor memory unit according to signal types in the above first embodiment;

FIG. 5 is a table showing a specific example of judgement information stored in the processor memory unit and the endoscope memory unit in the above first embodiment; and FIG. 6 is a flowchart showing operation of the processor in the endoscope apparatus according to the above first embodiment.

DETAILED DESCRIPTION OF THE PREFERRED EMBODIMENT

In the following, an embodiment of the present invention is explained with reference to the drawings.

Figure 1:
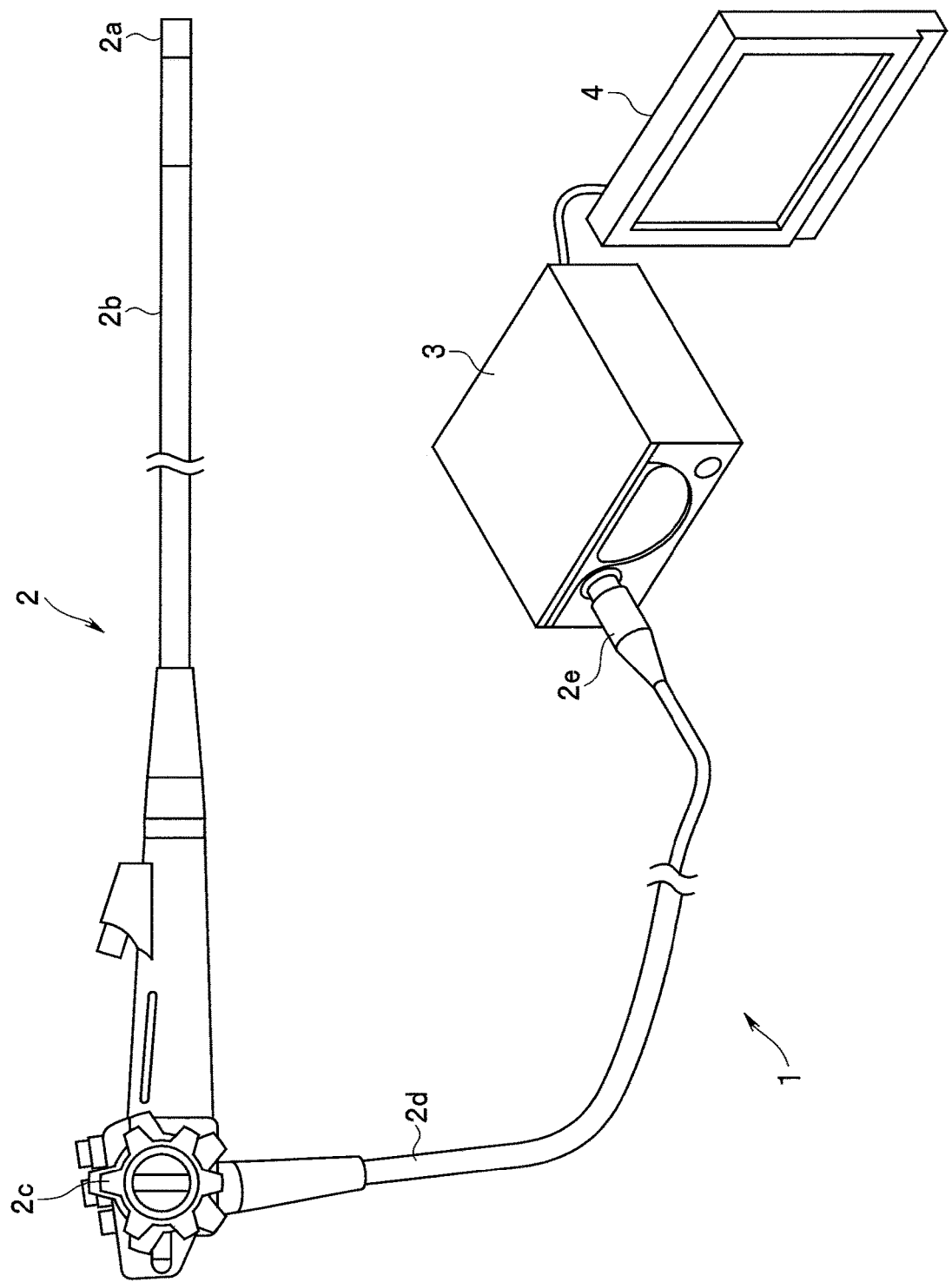
FIG. 1 shows an external appearance of an endoscope apparatus according to a first embodiment of the present invention.

FIG. 1 to FIG. 6 show a first embodiment of the present invention, and FIG. 1 shows an external appearance of an endoscope apparatus 1.

The endoscope apparatus 1 according to the present embodiment includes an endoscope 2 and a processor 3 to which the endoscope 2 is connected, and further includes, for example, a monitor 4 connected to the processor 3. However, the monitor 4 does not need to have a configuration specific to the endoscope apparatus 1 and a monitor provided separately from the endoscope apparatus 1 may also be used.

The endoscope 2 is introducible into a subject and used for optical observation inside the subject. Here, a subject into which the endoscope 2 is introduced may be any one of a human body, a living body other than a human body, an artifact such as a machine and a building, and the like.

It is also assumed in the present embodiment that the endoscope 2 is, but not limited to, an electronic endoscope configured to pick up optical images of a subject. The endoscope 2 may also be, for example, an optical endoscope.

The endoscope 2 includes an insertion section 2b equipped with a distal end section 2a on a distal end side, an operation section 2c positioned at a proximal end of the insertion section 2b, a universal cord 2d extending from a side portion of the operation section 2c, and a connector section 2e arranged at an end portion of the universal cord 2d.

In the distal end section 2a, an image pickup unit 23 including a lens 21 and an image pickup device 22 to be described later (see FIG. 2, etc.) is arranged to capture optical images of a subject. In the distal end section 2a, an actuator 24 to be described later (see FIG. 2, etc.) is also arranged to drive the lens 21. Further, even though it is not shown, an illumination optical system to irradiate a subject with illumination light and other components are also arranged in the distal end section 2a.

The insertion section 2b is a part that is introduced into a subject. Here, the insertion section 2b may be either a soft type with flexibility or a hard type without flexibility. The insertion section 2b may also have other components such as a bending portion to change a direction of the distal end section 2a. In the insertion section 2b, a signal line connected to the image pickup device 22, a signal line connected to the actuator 24, a light guide composed of components such as a fiber bundle which transmits illumination light, and the like are arranged.

The operation section 2c is a part to hold and operate the endoscope 2. When a bending portion is arranged in the insertion section 2b, operation to bend the bending portion is performed by an angle operation knob and the like arranged in the operation section 2c. Operation in connection with image pickup, operation in connection with air feeding/water feeding, and other operation can also be performed by an operation switch and the like arranged in the operation section 2c. Then, an endoscope memory unit 25 to be described later (see FIG. 2, etc.) and configured to store information on the endoscope 2 is arranged in, for example, the operation section 2c (though not limited to the arrangement in the operation section 2c).

The universal cord 2d and the connector section 2e are portions to connect the endoscope 2 to the processor 3. In the universal cord 2d and the connector section 2e, components such as the signal lines and the light guide as stated above are arranged.

Then, the endoscope 2 is electrically and optically connected to the processor 3 by connecting the connector section 2e to a connector receiver of the processor 3.

The processor 3 controls the endoscope 2 and applies image processing to image pickup signals received from the image pickup device 22 of the endoscope 2 to generate image signals for display and image signals for recording. The processor 3 also includes, for example, a light source device in the inside to supply illumination light to the light guide (though, of course, the light source device may be provided separately from the processor 3). The processor 3 further includes an actuator driving circuit 34 to be described later (see FIG. 2, etc.) as a driving circuit to drive the actuator 24 of the endoscope 2 as stated above.

The monitor 4 is connected to the processor 3 via a monitor cable. Then, the monitor 4 receives image signals for display from the processor 3, displays endoscope images, and further displays information associated with the endoscope 2 and the processor 3, and the like.

Figure 2:
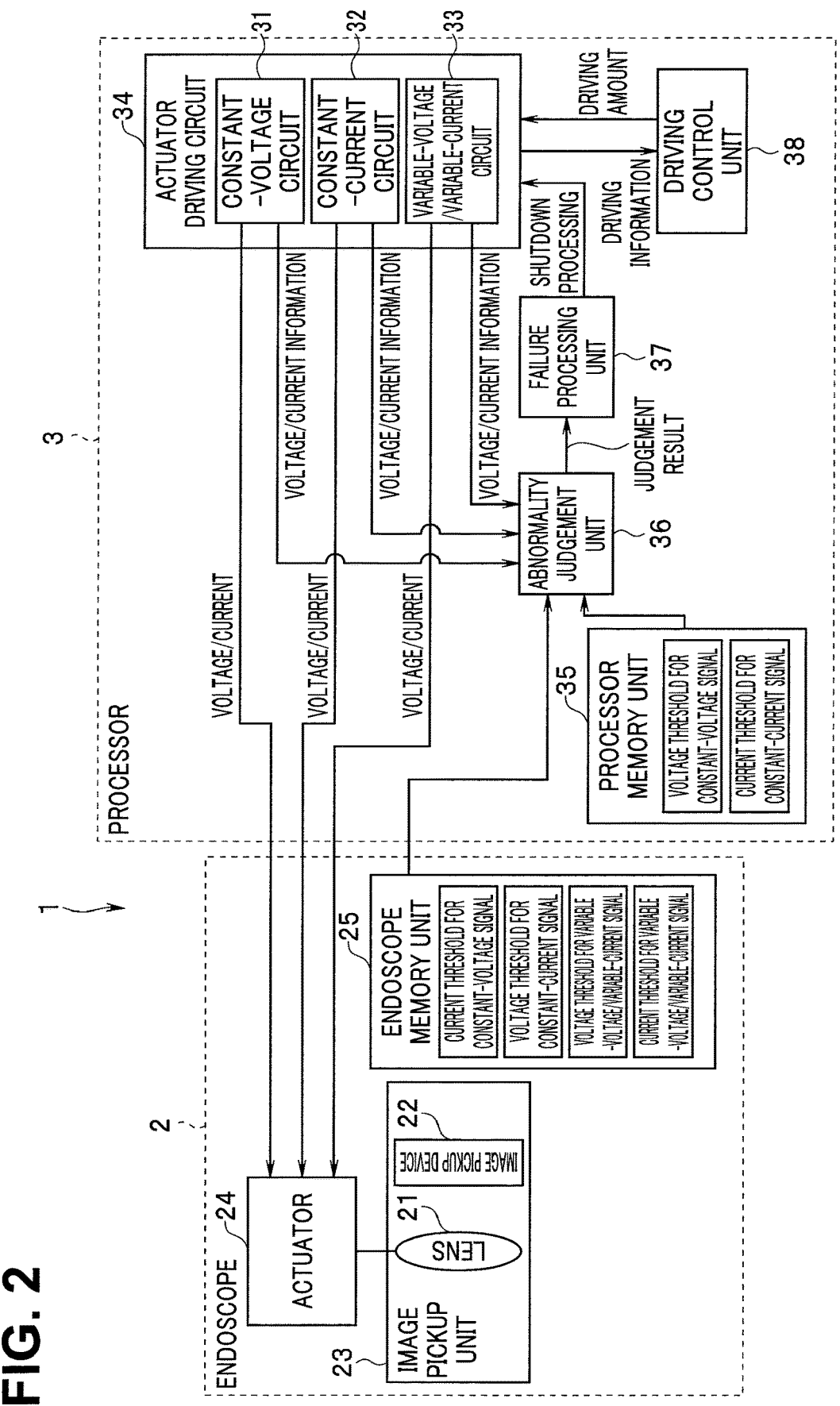
FIG. 2 is a block diagram showing a basic configuration of the endoscope apparatus in the above first embodiment.

FIG. 2 is a block diagram showing a basic configuration of the endoscope apparatus 1. Note that, as stated above, the monitor 4 is not an essential component of the endoscope apparatus 1 and therefore not specifically shown in FIG. 2 and FIG. 3 or other figures to be described later.

The endoscope 2 has the image pickup unit 23 including the lens 21 and the image pickup device 22, the actuator 24 configured to drive the lens 21, and the endoscope memory unit 25.

The lens 21 forms optical images of a subject and forms the images on an image pickup surface of the image pickup device 22. The lens 21 is generally composed of a plurality of lens groups and, for example, at least one lens group is movable in an optical axis direction. More specifically, when the lens 21 can be subjected to, for example, focus adjustment, a lens group associated with focus is movable. Besides, when the lens 21 can be, for example, zoomed in/out, a lens group associated with zoom is movable. Accordingly, the lens 21 is configured as an objective optical system which enables, for example, at least one of focus or zoom. Additionally, in the lens 21, an optical aperture not shown is also arranged.

The image pickup device 22 applies photoelectric conversion to optical images of a subject formed by the lens 21 to generate electrical image pickup signals. Image pickup signals thus generated here are transmitted to the processor 3 and subjected to image processing as stated above.

The actuator 24 causes at least one lens group of the lens 21 to move in the optical axis direction to perform at least one of focus operation or zoom operation.

The endoscope memory unit 25 serves as a first memory unit (first memory) composed of a non-volatile memory and other components and configured to store information relevant to the endoscope 2. The endoscope memory unit 25 stores first judgement information for use in judging abnormality of at least one of the actuator 24 or the actuator driving circuit 34. More specifically, the endoscope memory unit 25 stores, as first judgement information, a current threshold for constant-voltage signal (first current threshold), a voltage threshold for constant-current signal (second voltage threshold), a voltage threshold for variable-voltage/variable-current signal (third voltage threshold), and a current threshold for variable-voltage/variable-current signal (third current threshold).

Here, FIG. 4 provides a table showing judgement information stored in the endoscope memory unit 25 and a processor memory unit 35 according to signal types.

The current threshold for constant-voltage signal is a threshold for use in judging abnormality of a current of a constant-voltage signal (first signal) transmitted from the actuator driving circuit 34 to the actuator 24.

The voltage threshold for constant-current signal is a threshold for use in judging abnormality of a voltage of a constant-current signal (second signal) transmitted from the actuator driving circuit 34 to the actuator 24.

The voltage threshold for variable-voltage/variable-current signal is a threshold for use in judging abnormality of a voltage of a variable-voltage/variable-current signal (third signal) transmitted from the actuator driving circuit 34 to the actuator 24.

The current threshold for variable-voltage/variable-current signal is a threshold for use in judging abnormality of a current of the above variable-voltage/variable-current signal.

The endoscope memory unit 25 further stores general information relevant to the endoscope 2 including, for example, a model number and a production number of the endoscope 2, information relevant to the image pickup unit 23, and other information.

The processor 3 has the actuator driving circuit 34 including a constant-voltage circuit 31, a constant-current circuit 32, and a variable-voltage/variable-current circuit 33, the processor memory unit 35, an abnormality judgement unit 36, a failure processing unit 37, and a driving control unit 38.

The actuator driving circuit 34 is a driving circuit to drive the actuator 24 of the endoscope 2 by transmitting signals to the actuator 24. The actuator driving circuit 34 grasps a state of the lens 21 driven by the actuator 24 or more specifically a driving position of the lens 21 and the like, and transmits information thus grasped as driving information to the driving control unit 38.

The constant-voltage circuit 31 supplies a signal having a constant voltage (constant-voltage signal) to the actuator 24. The constant-voltage circuit 31 transmits, to the abnormality judgement unit 36, information on a voltage value and a current value of the constant-voltage signal supplied to the actuator 24.

The constant-current circuit 32 supplies a signal having a constant current (constant-current signal) to the actuator 24. The constant-current circuit 32 transmits, to the abnormality judgement unit 36, information on a voltage value and a current value of the constant-current signal supplied to the actuator 24.

The variable-voltage/variable-current circuit 33 supplies a signal having a variable voltage and a variable current (variable-voltage/variable-current signal) to the actuator 24. The variable-voltage/variable-current circuit 33 transmits, to the abnormality judgement unit 36, information on a voltage value and a current value of the variable-voltage/variable-current signal supplied to the actuator 24.

The processor memory unit 35 is a second memory unit (second memory) composed of a non-volatile memory and other components and configured to store information relevant to the processor 3. The processor memory unit 35 stores second judgement information for use in judging abnormality of at least one of the actuator 24 or the actuator driving circuit 34. Here, the second judgement information is information different from the first judgement information stated above. More specifically, the processor memory unit 35 stores, as the second judgement information, a voltage threshold for constant-voltage signal (first voltage threshold) and a current threshold for constant-current signal (second current threshold) as also shown in FIG. 4.

Here, the voltage threshold for constant-voltage signal is a threshold for use in judging abnormality of a voltage of the constant-voltage signal (first signal) stated above.

The current threshold for constant-current signal is a threshold for use in judging abnormality of a current of the constant-current signal (second signal) stated above.

The processor memory unit 35 further stores general information relevant to the processor 3 including, for example, information on a model number and a production number of the processor 3.

As shown in FIG. 4, the first judgement information stored in the endoscope memory unit 25 and the second judgement information stored in the processor memory unit 35 are classified according to signal types, namely the constant-voltage signal, the constant-current signal, and the variable-voltage/variable-current signal. The classification is based on whether a voltage value and a current value of a signal transmitted from the actuator driving circuit 34 to the actuator 24 are determined dominantly in the processor 3 or determined dominantly in the endoscope 2.

In the case of the constant-voltage signal, a current value is determined dominantly by a load of the actuator 24 and accuracy of a voltage value is determined dominantly according to a design of the actuator driving circuit 34. Therefore, information on the current threshold for constant-voltage signal (first current threshold) in connection with current abnormality is stored as the first judgement information in the endoscope memory unit 25, and information on the voltage threshold for constant-voltage signal (first voltage threshold) in connection with voltage abnormality is stored as the second judgement information in the processor memory unit 35.

In the case of the constant-current signal, accuracy of a current value is determined dominantly according to a design of the actuator driving circuit 34 of the processor 3 and a voltage value is determined dominantly by a load of the actuator 24. Therefore, information on the current threshold for constant-current signal (second current threshold) in connection with current abnormality is stored as the second judgement information in the processor memory unit 35, and information on the voltage threshold for constant-current signal (second voltage threshold) in connection with voltage abnormality is stored as the first judgement information in the endoscope memory unit 25.

In the case of the variable-voltage/variable-current signal, a voltage value and a current value are determined dominantly by a load of the actuator 24. Therefore, information on the voltage threshold for variable-voltage/variable-current signal (third voltage threshold) in connection with voltage abnormality and information on the current threshold for variable-voltage/variable-current signal (third current threshold) in connection with current abnormality are stored as the first judgement information in the endoscope memory unit 25.

The abnormality judgement unit 36 is an abnormality judgement circuit configured to judge whether there is abnormality or not in at least one of the actuator 24 or the actuator driving circuit 34 by using information on the signal transmitted from the actuator driving circuit 34 to the actuator 24, the first judgement information read from the endoscope memory unit 25, and the second judgement information read from the processor memory unit 35.

More specifically, the abnormality judgement unit 36 judges whether there is abnormality or not in at least one of the actuator 24 or the actuator driving circuit 34 by obtaining at least one of a current value or a voltage value (preferably both a current value and a voltage value) of the signal transmitted from the actuator driving circuit 34 to the actuator 24 and comparing at least one of the current value or the voltage value with the first judgement information or the second judgement information.

For example, when the abnormality judgement unit 36 obtains a voltage value of a constant-voltage signal received from the constant-voltage circuit 31, the abnormality judgement unit 36 compares the voltage value with the voltage threshold for constant-voltage signal read from the processor memory unit 35. If the voltage value of the constant-voltage signal is greater than the voltage threshold for constant-voltage signal, the abnormality judgement unit 36 judges that there is abnormality in at least one of the actuator 24 or the actuator driving circuit 34.

Also, when the abnormality judgement unit 36 obtains a current value of a constant-voltage signal received from the constant-voltage circuit 31, the abnormality judgement unit 36 compares the current value with the current threshold for constant-voltage signal read from the endoscope memory unit 25. If the current value of the constant-voltage signal is greater than the current threshold for constant-voltage signal, the abnormality judgement unit 36 judges that there is abnormality in at least one of the actuator 24 or the actuator driving circuit 34.

Further, when the abnormality judgement unit 36 obtains a voltage value of a constant-current signal received from the constant-current circuit 32, the abnormality judgement unit 36 compares the voltage value with the voltage threshold for constant-current signal read from the endoscope memory unit 25. If the voltage value of the constant-current signal is greater than the voltage threshold for constant-current signal, the abnormality judgement unit 36 judges that there is abnormality in at least one of the actuator 24 or the actuator driving circuit 34.

Then, when the abnormality judgement unit 36 obtains a current value of a constant-current signal received from the constant-current circuit 32, the abnormality judgement unit 36 compares the current value with the current threshold for constant-current signal read from the processor memory unit 35. If the current value of the constant-current signal is greater than the current threshold for constant-current signal, the abnormality judgement unit 36 judges that there is abnormality in at least one of the actuator 24 or the actuator driving circuit 34.

In addition, when the abnormality judgement unit 36 obtains a voltage value of a variable-voltage/variable-current signal received from the variable-voltage/variable-current circuit 33, the abnormality judgement unit 36 compares the voltage value with the voltage threshold for variable-voltage/variable-current signal read from the endoscope memory unit 25. If the voltage value of the variable-voltage/variable-current signal is greater than the voltage threshold for variable-voltage/variable-current signal, the abnormality judgement unit 36 judges that there is abnormality in at least one of the actuator 24 or the actuator driving circuit 34.

Similarly, when the abnormality judgement unit 36 obtains a current value of a variable-voltage/variable-current signal received from the variable-voltage/variable-current circuit 33, the abnormality judgement unit 36 compares the current value with the current threshold for variable-voltage/variable-current signal read from the endoscope memory unit 25. If the current value of the variable-voltage/variable-current signal is greater than the current threshold for variable-voltage/variable-current signal, the abnormality judgement unit 36 judges that there is abnormality in at least one of the actuator 24 or the actuator driving circuit 34.

When the abnormality judgement unit 36 judges that there is certain abnormality, the abnormality judgement unit 36 transmits a judgement result to the failure processing unit 37.

When the failure processing unit 37 receives a judgement result indicating that there is abnormality from the abnormality judgement unit 36, the failure processing unit 37 performs shutdown processing and transmits a control signal for use in stopping driving of the actuator 24 to the actuator driving circuit 34. Therefore, signal transmission from the actuator driving circuit 34 to the actuator 24 is stopped to stop driving the actuator 24.

The driving control unit 38 receives driving information of the actuator 24 from the actuator driving circuit 34, sets a driving amount so that the lens 21 moves to a target position, and transmits the set driving amount to the actuator driving circuit 34 which is thus made to perform a driving control. The driving control unit 38 thus performs a feedback control for the actuator 24 via the actuator driving circuit 34.

Figure 3:
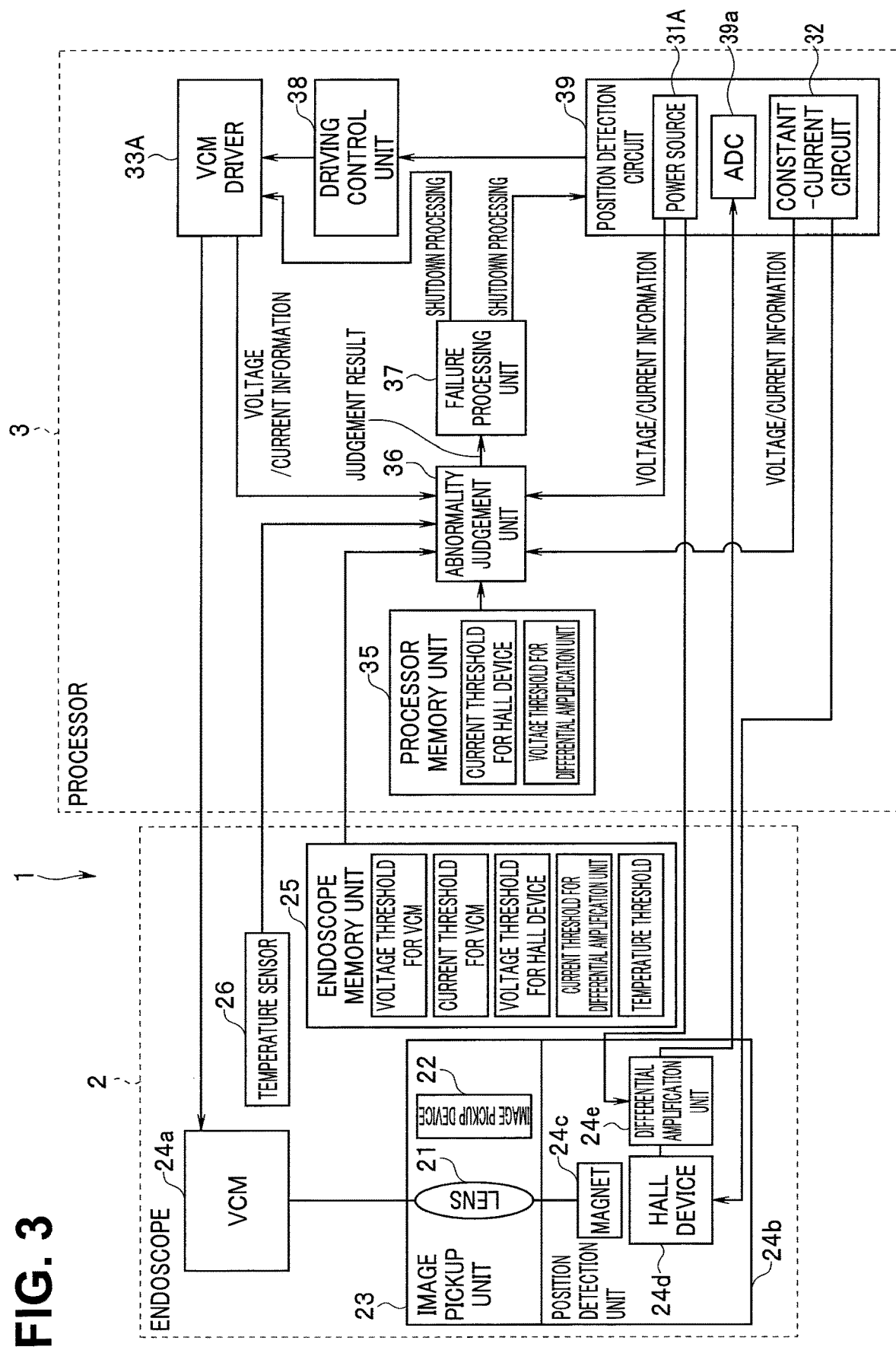
FIG. 3 is a block diagram showing a specific configuration example of the endoscope apparatus in the above first embodiment.

FIG. 3 is a block diagram showing a specific configuration example of the endoscope apparatus 1. The endoscope apparatus 1 shown in FIG. 3 represents a more specific configuration of the endoscope apparatus 1 shown in FIG. 2.

The actuator 24 of the endoscope 2 includes a voice coil motor (VCM) 24a serving as a motor configured to drive the lens 21, and a position detection unit 24b (position detector) to detect a position of the lens 21 driven by the VCM 24a.

The VCM 24a is a linear actuator configured to drive the lens 21 in the optical axis direction. The VCM 24a is driven through transmission of the variable-voltage/variable-current signal as shown in FIG. 4.

The position detection unit 24b includes a magnet 24c that moves integrally with the lens 21 in the optical axis direction, a Hall device 24d configured to detect a position of the magnet 24c in the optical axis direction and consequently a position of the lens 21 in the optical axis direction by detecting a magnetic field generated from the magnet 24c, and a differential amplification unit 24e (differential amplifier) composed of an operational amplifier configured to amplify signals outputted from the Hall device 24d.

The position detection unit 24b is driven through transmission of the constant-voltage signal and the constant-current signal. More specifically, as shown in FIG. 4, the Hall device 24d is driven through transmission of the constant-current signal and the differential amplification unit 24e is driven through transmission of the constant-voltage signal.

In the vicinity of the VCM 24a, a temperature sensor 26 configured to detect a temperature of the VCM 24a is arranged.

The endoscope memory unit 25 stores a current threshold for differential amplification unit as the current threshold for constant-voltage signal, a voltage threshold for Hall device as the voltage threshold for constant-current signal, a voltage threshold for VCM as the voltage threshold for variable-voltage/variable-current signal, and a current threshold for VCM as the current threshold for variable-voltage/variable-current signal.

Here, FIG. 5 provides a table showing specific examples of judgement information stored in the processor memory unit 35 and the endoscope memory unit 25.

Further, the endoscope memory unit 25 stores, as the first judgement information, a temperature threshold for use in judging whether heat generation in the VCM 24a is abnormal or not based on a temperature detected by the temperature sensor 26.

Then, the abnormality judgement unit 36 obtains temperature information from the temperature sensor 26 and compares a temperature indicated in the temperature information with the temperature threshold, whereby judging whether there is abnormality or not in at least one of the actuator 24 or the actuator driving circuit 34.

In other words, the abnormality judgement unit 36 compares a temperature indicated in the temperature information obtained from the temperature sensor 26 with the temperature threshold read from the endoscope memory unit 25. If the temperature indicated in the temperature information is higher than the temperature threshold, the abnormality judgement unit 36 judges that there is abnormality in at least one of the actuator 24 or the actuator driving circuit 34.

The processor memory unit 35 of the processor 3 stores a voltage threshold for differential amplification unit as the voltage threshold for constant-voltage signal, and a current threshold for Hall device as the current threshold for constant-current signal.

The processor 3 includes a VCM driver 33A as a specific example of the variable-voltage/variable-current circuit 33 shown in FIG. 2. The VCM driver 33A drives the VCM 24a by transmitting a variable-voltage/variable-current signal to the VCM 24a. Then, the VCM driver 33A transmits, to the abnormality judgement unit 36, information on a voltage value and a current value of the variable-voltage/variable-current signal supplied to the VCM 24a.

The processor 3 also includes a position detection circuit 39 configured to obtain a position detection result from the position detection unit 24b by supplying power to the position detection unit 24b.

The position detection circuit 39 includes a constant-current circuit 32, and the constant-current circuit 32 drives the Hall device 24d. The constant-current circuit 32 transmits, to the abnormality judgement unit 36, information on a voltage value and a current value of the constant-current signal supplied to the Hall device 24d.

The position detection circuit 39 also includes, as a specific example of the constant-voltage circuit 31, a power source 31A configured to drive the differential amplification unit 24e. The power source 31A transmits, to the abnormality judgement unit 36, information on a voltage value and a current value of the constant-voltage signal supplied to the differential amplification unit 24e.

The position detection circuit 39 further includes an analog digital converter (ADC) 39a configured to convert an analog signal outputted from the Hall device 24d and amplified by the differential amplification unit 24e into a digital signal. The position detection circuit 39 generates positional information of the lens 21 based on the signal digitized by the ADC 39a and transmits the positional information to the driving control unit 38.

The driving control unit 38 obtains the positional information of the lens 21 from the position detection circuit 39 and transmits a command to the VCM driver 33A so that the lens 21 moves to a target position, whereby causing the VCM 24a to be driven. The lens 21 is thus driven and subjected to at least one of focus adjustment or zoom adjustment.

When the failure processing unit 37 receives a judgement result indicating that there is abnormality from the abnormality judgement unit 36, the failure processing unit 37 performs shutdown processing, transmits a control signal for use in stopping driving of the VCM 24a to the VCM driver 33A, and transmits a control signal for use in stopping operation of the position detection unit 24b to the position detection circuit 39. Therefore, driving and position detection of the lens 21 are discontinued.

Additionally, FIG. 5 shows examples of not only respective thresholds (voltage thresholds, current thresholds, and temperature threshold) but also durations stored as the judgement information for use in judging abnormality.

The abnormality judgement unit 36 judges that there is abnormality in at least one of the actuator 24 or the actuator driving circuit 34 if a voltage value or a current value to drive the actuator 24 is greater than the threshold, as stated above.

However, when a voltage value or a current value is greater than the threshold only for a very short time and then maintained to fall below the threshold, such a state does not lead to stop driving of the actuator 24.

Therefore, a duration may be set to make the abnormality judgement unit 36 judge that there is abnormality if a state in which a voltage value or a current value is greater than a threshold continues for a longer period than the duration. The same time period may also be set as the duration for respective thresholds, though setting individual durations for respective thresholds enables more accurate abnormality judgement.

Hence, FIG. 5 shows examples of individual durations set for respective thresholds.

In other words, a duration for voltage in the VCM is set to the voltage threshold for VCM, a duration for current in the VCM is set to the current threshold for VCM, a duration for voltage in the Hall device is set to the voltage threshold for Hall device, a duration for current in the differential amplification unit is set to the current threshold for differential amplification unit, a duration for temperature is set to the temperature threshold, a duration for current in the Hall device is set to the current threshold for Hall device, and a duration for voltage in the differential amplification unit is set to the voltage threshold for differential amplification unit.

Accordingly, in an example case where a duration for which a voltage value of a signal transmitted from the VCM driver 33A to the VCM 24a exceeds the voltage threshold for VCM is beyond the duration for voltage in the VCM, the abnormality judgement unit 36 judges that there is abnormality. This also applies to other durations.

FIG. 6 is a flowchart showing operation of the processor 3 in the endoscope apparatus 1.

When the processor 3 in a state of being connected to the endoscope 2 is activated or the processor 3 in a state of being activated is connected to the endoscope 2, the process is made to start.

At the point of beginning the process, the processor 3 does not read at least the first judgement information from the endoscope memory unit 25 yet. Further, when the processor 3 itself is activated and then the process is made to start, the processor 3 does not read the second judgement information from the processor memory unit 35 yet.

Therefore, in initial setting of each threshold serving as judgement information, the abnormality judgement unit 36 of the processor 3 firstly sets each threshold to a value that is less than a value of the first judgement information stored in the endoscope memory unit 25 and less than a value of the second judgement information stored in the processor memory unit 35 (step S1).

Note that an initial value set for each threshold here is predetermined to be less than any values of the first judgement information and the second judgement information in any combinations of the processor 3 and various kinds of the endoscope 2.

Next, the abnormality judgement unit 36 of the processor 3 reads and receives respective thresholds serving as the first judgement information from the endoscope memory unit 25 (step S2).

Then, the abnormality judgement unit 36 judges whether the first judgement information was received normally from the endoscope memory unit 25 or not (step S3).

Here, if the abnormality judgement unit 36 judges that the first judgement information was not received normally, the abnormality judgement unit 36 transmits a judgement result indicating that there is abnormality to the failure processing unit 37. Therefore, the failure processing unit 37 performs shutdown processing to prohibit the actuator 24 from being driven. Note that abnormality here relates to the actuator 24 and the actuator driving circuit 34 so that image pickup operation by the image pickup device 22 and the like may be executed as usual.

If it is determined by the abnormality judgement unit 36 at step S3 that the first judgement information was received normally, the abnormality judgement unit 36 sets, in place of respective thresholds initially set at step S1, the respective thresholds received from the endoscope memory unit 25, and sets the respective thresholds read from the processor memory unit 35, after which the actuator driving circuit 34 is made to start driving the actuator 24 (step S4).

Then, the abnormality judgement unit 36 obtains information on voltage values and current values of signals (constant-voltage signal, constant-current signal, and variable-voltage/variable-current signal) transmitted from the actuator driving circuit 34 to the actuator 24 and judges whether any one of the voltage values or the current values exceeds the corresponding threshold or not (step S5).

Further, at step S5, the abnormality judgement unit 36 obtains temperature information from the temperature sensor 26 and judges whether a temperature indicated in the obtained temperature information exceeds the temperature threshold or not.

If it is judged by the abnormality judgement unit 36 at step S5 that any one of the voltage values, the current values, and the temperature exceeds any one of the corresponding thresholds, the abnormality judgement unit 36 further judges whether a time period in which any of a voltage value, a current value, or a temperature exceeds a threshold exceeds a corresponding duration or not (step S6).

Here, if it is judged by the abnormality judgement unit 36 that a time period in which the voltage values, the current values, or the temperature exceeds the threshold does not exceed the durations, the process returns to step S5 at which the abnormality judgement unit 36 continuously judges whether a voltage value, a current value, or a temperature exceeds the threshold or not.

Thus, if it is judged by the abnormality judgement unit 36 at step S6 that a time period in which any one of the voltage values, the current values, or the temperature exceeds the corresponding threshold exceeds the durations, the abnormality judgement unit 36 judges that there is abnormality and transmits a judgement result to the failure processing unit 37 (step S7). Therefore, the failure processing unit 37 performs the shutdown processing in failure as stated above to discontinue driving of the actuator 24.

In contrast, if it is judged by the abnormality judgement unit 36 at step S5 that the voltage values, the current values, and the temperature do not exceed the thresholds, the processor 3 judges whether to finish the process or not (step S8). If the processor 3 judges that the process is not finished, the process returns to step S5 at which the abnormality judgement unit 36 continuously judges whether any one of the voltage values, the current values, and the temperature exceeds the corresponding threshold or not.

Then, if it is judged by the processor 3 at step S8 that the process is finished, the process is finished.

Note that the abnormality judgement unit 36 stated above is configured to, but not limited to, judge the presence or absence of abnormality by obtaining a voltage value and a current value of a variable-voltage/variable-current signal transmitted from the actuator driving circuit 34 to the actuator 24 and comparing the voltage value and the current value with the voltage threshold for variable-voltage/variable-current signal and the current threshold for variable-voltage/variable-current signal.

For example, the abnormality judgement unit 36 may be configured to judge whether there is abnormality or not in at least one of the actuator 24 or the actuator driving circuit 34 by obtaining a power value of a variable-voltage/variable-current signal transmitted from the actuator driving circuit 34 to the actuator 24 and comparing the power value with a power threshold for variable-voltage/variable-current signal.

In this case, the endoscope memory unit 25 needs to store the first judgement information including the power threshold for variable-voltage/variable-current signal for use in judging abnormality of power of the variable-voltage/variable-current signal transmitted from the actuator driving circuit 34 to the actuator 24.

According to the first embodiment as such, the first judgement information is stored in the endoscope memory unit 25, the second judgement information is stored in the processor memory unit 35, and the abnormality judgement unit 36 judges whether there is abnormality or not in at least one of the actuator 24 or the actuator driving circuit 34 by using the first judgement information and the second judgement information, whereby enabling appropriate judgement of abnormality corresponding to any combinations of various types of endoscope and various types of processors.

The current threshold for the constant-voltage signal and the voltage threshold for the constant-current signal which are determined dominantly by a load of the actuator 24 are stored in the endoscope memory unit 25, and the voltage threshold for constant-voltage signal and the current threshold of constant-current signal, which are determined dominantly by a design of the actuator driving circuit 34, are stored in the processor memory unit 35, whereby allowing the abnormality judgement unit 36 to judge abnormality more appropriately corresponding to whether a signal is a constant-voltage signal or a constant-current signal.

The voltage threshold and the current threshold for the variable-voltage/variable-current signal which are determined dominantly by a load of the actuator 24 are stored in the endoscope memory unit 25, whereby allowing the abnormality judgement unit 36 to judge abnormality appropriately when a signal is a variable-voltage/variable-current signal.

The temperature sensor 26 is arranged in the vicinity of the actuator 24 and the temperature threshold is stored in the endoscope memory unit 25, whereby allowing the abnormality judgement unit 36 to appropriately judge abnormality of heat generation in the actuator 24.

As a specific configuration, when the actuator 24 includes the VCM 24a to which a variable-voltage/variable-current signal is transmitted, and the position detection unit 24b to which a constant-voltage signal and a constant-current signal are transmitted, the endoscope memory unit 25 stores a voltage threshold and a current threshold relevant to the VCM 24a, a current threshold relevant to the constant-voltage signal, and a voltage threshold relevant to the constant-current signal, and the processor memory unit 35 stores a voltage threshold relevant to the constant-voltage signal and a current threshold relevant to the constant-current signal, whereby the abnormality judgement unit 36 can make an appropriate judgement of abnormality.

Particularly in the configuration in which the position detection unit 24b includes the Hall device 24d to which a constant-current signal is transmitted and the differential amplification unit 24e to which a constant-voltage signal is transmitted, the endoscope memory unit 25 stores a current threshold relevant to the differential amplification unit 24e and a voltage threshold relevant to the Hall device 24d, and the processor memory unit 35 stores a voltage threshold relevant to the differential amplification unit 24e and a current threshold relevant to the Hall device 24d, whereby the abnormality judgement unit 36 can make an appropriate judgement of abnormality.

Additionally, by making the endoscope memory unit 25 store a power threshold for variable-voltage/variable-current signal and making the abnormality judgement unit 36 obtain a power value of the variable-voltage/variable-current signal and compare the power value with the power threshold for variable-voltage/variable-current signal, the abnormality judgement unit 36 is also allowed to appropriately judge whether there is abnormality or not in at least one of the actuator 24 or the actuator driving circuit 34.

Then, if reading the first judgement information from the endoscope memory unit 25 results in a failure, driving of the actuator 24 is prohibited, whereby enabling prevention of operation of the actuator 24 in an abnormal state.

Further, before the first judgement information is read from the endoscope memory unit 25 and the second judgement information is read from the processor memory unit 35, judgement information for use in judging abnormality of at least one of the actuator 24 or the actuator driving circuit 34 is set to a value less than a value of the first judgement information and a value of the second judgement information, whereby enabling prevention of judging an abnormal state as a normal state before reading the first judgement information and the second judgement information.

Note that the process in each unit as stated above may also be performed by one or more processors configured as hardware. For example, each unit may be a processor configured as an electronic circuit, or may be each circuit unit in a processor composed of an integrated circuit such as FPGA (Field Programmable Gate Array). Alternatively, a processor composed of one or more CPU may be configured to execute a function of each unit by reading and executing a processing program recorded in a recording medium.

In addition, even though the above explanation is directed mainly to the case where the present invention is the endoscope apparatus, the present invention may also be an operation method to operate the endoscope apparatus as stated above, a processing program to make a computer perform the same process as the process of the endoscope apparatus, a non-transitory recording medium recording the processing program that is readable by a computer, and the like.

Further, the present invention is not limited to the above-stated embodiment as it is but may be carried out by modifying constituent elements within a range that does not depart from the gist of the invention in the implementation phase. Various modes of the invention may also be formed by appropriate combinations of a plurality of constituent elements disclosed in the above embodiment. For example, some of constituent elements may be removed from all the constituent elements presented in the embodiment. Further, constituent elements may also be combined appropriately across different embodiments. Thus, as a matter of course, various modifications and applications are possible within the range that does not depart from the gist of the invention.

What is claimed is:
1. An endoscope apparatus comprising:
an endoscope:
a processor to which the endoscope is connected:
a lens arranged in the endoscope:
an actuator arranged in the endoscope and configured to drive the lens:
a driving circuit arranged in the processor and configured to drive the actuator by transmitting a signal to the actuator:
a first memory arranged in the endoscope and configured to store first judgement information for use in judging an abnormality of at least one of the actuator or the driving circuit, the first memory being configured to store the first judgement information including a first current threshold for use in judging the abnormality of a current of a first signal having a constant voltage and transmitted from the driving circuit to the actuator, and a second voltage threshold for use in judging the abnormality of a voltage of a second signal having a constant current and transmitted from the driving circuit to the actuator; and
a second memory arranged in the processor and configured to store second judgement information for use in judging the abnormality of at least one of the actuator or the driving circuit, the second judgement information being different from the first judgement information, the second memory being configured to store the second judgement information including a first voltage threshold for use in judging the abnormality of a voltage of the first signal, and a second current threshold for use in judging the abnormality of a current of the second signal, wherein
the processor judges whether there is the abnormality or not in at least one of the actuator or the driving circuit by using information on the first signal or the second signal transmitted from the driving circuit to the actuator, the first judgement information read from the first memory, and the second judgement information read from the second memory, and
the processor obtains at least one of a current value or a voltage value of the signal transmitted from the driving circuit to the actuator, and
when obtaining a current value of the first signal, the processor compares the obtained current value of the first signal with the first current threshold and judges that the abnormality exists when the current value of the first signal exceeds the first current threshold,
when obtaining a voltage value of the first signal, the processor compares the obtained voltage value of the first signal with the first voltage threshold and judges that the abnormality exists when the voltage value of the first signal exceeds the first voltage threshold,
when obtaining a voltage value of the second signal, the processor compares the obtained voltage value of the second signal with the second voltage threshold and judges that the abnormality exists when the voltage value of the second signal exceeds the second voltage threshold, or
when obtaining a current value of the second signal, the processor compares the obtained current value of the second signal with the second current threshold and judges that the abnormality exists when the current value of the second signal exceeds the second current threshold.
2. The endoscope apparatus according to claim 1, wherein the first memory stores the first judgement information including a third voltage threshold for use in judging the abnormality of a voltage of a third signal having a variable voltage and a variable current and transmitted from the driving circuit to the actuator, and a third current threshold for use in judging the abnormality of a current of the third signal, and the processor judges whether the abnormality exists or not by obtaining at least one of the current value or the voltage value transmitted from the driving circuit to the actuator, and when obtaining a voltage value of the third signal, comparing the obtained voltage value of the third signal with the third voltage threshold or when obtaining a current value of the third signal, comparing the obtained current value of the third signal with the third current threshold.

3. The endoscope apparatus according to claim 2, wherein the actuator includes a motor configured to drive the lens, and a position detector configured to detect a position of the lens driven by the motor, the third signal is transmitted to the motor, and the first signal and the second signal are transmitted to the position detector.

4. The endoscope apparatus according to claim 3, wherein the position detector includes a Hall device and a differential amplifier, the second signal is transmitted to the Hall device, and the first signal is transmitted to the differential amplifier.

5. The endoscope apparatus according to claim 1, further comprising a temperature sensor arranged in a vicinity of the actuator, wherein the first memory stores the first judgement information including a temperature threshold for use in judging the abnormality of heat generation in the actuator, and the processor judges whether the abnormality exists or not by obtaining temperature information from the temperature sensor and comparing a temperature indicated in the temperature information with the temperature threshold.

6. The endoscope apparatus according to claim 1, wherein the first memory stores the first judgement information including a power threshold for use in judging the abnormality of power of a third signal having a variable voltage and a variable current and transmitted from the driving circuit to the actuator, and the processor judges whether the abnormality exists or not by obtaining a power value of the third signal transmitted from the driving circuit to the actuator and comparing the power value with the power threshold.

7. The endoscope apparatus according to claim 2, wherein when the processor in a state of being connected to the endoscope is activated or the processor in a state of being activated is connected to the endoscope, the processor reads the first judgement information from the first memory and prohibits the actuator from being driven in a case of failing to read the first judgement information.

8. The endoscope apparatus according to claim 1, wherein before the processor reads the first judgement information from the first memory and reads the second judgement information from the second memory, the processor sets judgement information for use in judging the abnormality of at least one of the actuator or the driving circuit to a value less than a value of the first judgement information and a value of the second judgement information.

9. The endoscope apparatus according to claim 1, wherein the processor obtains each of the current value and the voltage value transmitted from the driving circuit to the actuator.

10. An endoscope apparatus operation method comprising steps of:

causing an actuator arranged in an endoscope to drive a lens arranged in the endoscope;

causing a driving circuit arranged in a processor connected to the endoscope to drive the actuator by transmitting a signal to the actuator;

causing a first memory arranged in the endoscope to store first judgement information for use in judging an abnormality of at least one of the actuator or the driving circuit and causing the first memory to store the first judgement information including a first current threshold for use in judging the abnormality of a current of a first signal having a constant voltage and transmitted from the driving circuit to the actuator, and a second voltage threshold for use in judging the abnormality of a voltage of a second signal having a constant current and transmitted from the driving circuit to the actuator;

causing a second memory arranged in the processor to store second judgement information for use in judging the abnormality of at least one of the actuator or the driving circuit, the second judgement information being different from the first judgement information, and causing the second memory to store the second judgement information including a first voltage threshold for use in judging the abnormality of a voltage of the first signal, and a second current threshold for use in judging the abnormality of a current of the second signal;

causing the processor to judge whether there is the abnormality or not in at least one of the actuator or the driving circuit by using information on the first signal or the second signal transmitted from the driving circuit to the actuator, the first judgement information read from the first memory, and the second judgement information read from the second memory; and causing the processor to obtain at least one of a current value or a voltage value transmitted from the driving circuit to the actuator, and when obtaining a current value of the first signal, causing the processor to compare the obtained current value of the first signal with the first current threshold and judge that the abnormality exists when the current value of the first signal exceeds the first current threshold, when obtaining a voltage value of the first signal, causing the processor to compare the obtained voltage value of the first signal with the first voltage threshold and judge that the abnormality exists when the voltage value of the first signal exceeds the first voltage threshold, when obtaining a voltage value of the second signal, causing the processor to compare the obtained voltage value of the second signal with the second voltage threshold and judge that the abnormality exists when the voltage value of the second signal exceeds the second voltage threshold, or when obtaining a current value of the second signal, causing the processor to compare the obtained current value of the second signal with the second current threshold and judge that the abnormality exists when the current value of the second signal exceeds the second current threshold.

11. The endoscope apparatus according to claim 10, wherein the processor obtains each of the current value and the voltage value transmitted from the driving circuit to the actuator.

* * * * *